United States Patent [19]

Koontz et al.

[11] Patent Number: 4,805,070
[45] Date of Patent: Feb. 14, 1989

[54] CAPACITIVE COUPLED MOISTURE SENSOR

[75] Inventors: Harry S. Koontz, Penn Hills Township, Allegheny County; James F. Wilson, Worthington, both of Pa.

[73] Assignee: PPG Industries, Inc., Pittsburgh, Pa.

[21] Appl. No.: 111,323

[22] Filed: Oct. 22, 1987

[51] Int. Cl.[4] .......................... H01G 5/20; H01G 7/00
[52] U.S. Cl. ..................................... 361/286; 73/336.5
[58] Field of Search ...................... 73/336.5; 361/286; 324/60 C, 61 R

[56] References Cited

U.S. PATENT DOCUMENTS

| | | | |
|---|---|---|---|
| 3,986,110 | 10/1976 | Overall et al. | 324/61 R |
| 4,164,868 | 8/1979 | Suntola | 73/336.5 |
| 4,429,343 | 1/1984 | Freud | 361/286 |
| 4,520,341 | 5/1985 | Miyoshi et al. | 73/336.5 X |
| 4,522,060 | 6/1985 | Murata et al. | 73/336.5 |
| 4,639,831 | 1/1987 | Iyoda | 361/286 |

Primary Examiner—Donald A. Griffin
Attorney, Agent, or Firm—Andrew C. Siminerio

[57] ABSTRACT

A rain sensor for a windshield having two sets of electroconductive coatings on opposing major surfaces of the outer glass ply of a windshield. The first set of coatings on the outer major surface of the ply are electrically insulated from but in close proximity to each other. The second set of electroconductive coatings are positioned within the windshield between the glass plies and are electrically connected to a signal generator and receiver. Water contacting the outer surface of the glass ply changes the nature of an electrical signal passing through the first pair of electroconductive coatings. In response to the altered signal, a controller actuates a windshield wiper arrangement to clear the viewing area of the windshield.

31 Claims, 1 Drawing Sheet

CAPACITIVE COUPLED MOISTURE SENSOR

BACKGROUND OF THE INVENTION

1. Field of the Invention

This invention relates to a sensor for detecting moisture on a windshield, and in particular, to a sensor that automatically actuates a windshield wiper motor when water is detected on a windshield moisture sensor.

2A. Technical Considerations

The forward window of a vehicle, such as an automobile or aircraft, through which the operator views the outside world is generally referred to as a windshield. Vehicle windshields are generally of a laminated construction wherein multiple plies of glass and/or plastic are secured to one another by interlayer material. Because of the importance of maintaining a clear, undistorted viewing area through the windshield, wiper mechanisms are generally provided to clear selected portions of the windshield of water and/or dirt that may obscure the vehicle operator's vision.

Moisture sensors have been used to sense rain on windshields. The sensors may be connected to controls that automatically actuate the windshield wiper motors to remove the water and clear the vision area. The sensors generally include electrically conductive members with a protective coating on the exterior major surface of the windshield. The conduction members are arranged in a fixed relationship forming variable capacitors such that moisture on the protective coating alters the capacitance of the sensor's circuitry.

2B. Patents of Interest

U.S. Pat. No. 4,164,868 to Suntola teaches a capacitive humidity transducer wherein an electrically nonconductive base carries at least a pair of electrically conductive coatings which are spaced from each other along the major surface of the base. A dielectric film which is active with respect to water absorption is also carried by the base and covers at least a portion of the coatings. The dielectric film has a dielectric constant which varies as a function of the extent to which water has been absorbed by the film. An outer, electrically conductive, water-permeable layer is carried by the dielectric film. The dielectric film maintains the outer layer permanently out of contact with at least one of the coatings so that it is possible to measure a capacitance between these coatings, which will be indicative of atmospheric humidity.

U.S. Pat. No. 4,429,343 to Freud teaches a humidity-sensing element having two sets of interdigitated, thin film platinum fingers deposited on the surface of a glass substrate. The film is covered by a coating of water-absorbing material such as cellulose acetate butyrate or silicone rubber. The humidity sensitivity of the sensor arises from the humidity-related dielectric constant change which occurs in the coating over the fingers. As this dielectric constant changes, so does the capacitance between the interdigitated fingers.

U.S. Pat. No. 4,639,831 to Iyoda teaches a transparent sensor for detecting rain on window glass. The rain sensor is made from transparent material and is located within the wiping area on the exterior surface of the window glass. The sensor includes a pair of electrodes having interdigitated finger members that are insulated electrically from each other by a clearance. A transparent insulating protector film covers the electrodes and the clearance. The interdigitated members form capacitors having variable capacitance. When a drop of water is positioned on a portion of the protective coating defined between a pair of finger members, i.e., aligned with the clearance, the capacitance of the capacitor becomes greater than the normal capacitance because the dielectric constant of the drop of water is greater than the dielectric constant of air. Accordingly, when many drops of water are positioned on the protective coating, the total capacitance formed between the electrodes becomes larger.

SUMMARY OF THE INVENTION

An object of this invention is to provide a sensor to detect moisture on the surface of a substrate. In one particular embodiment of the invention, the substrate is a multilayered windshield which includes an inner and outer glass ply separated by an interlayer. First and second transparent, electroconductive coatings are secured to the outboard surface of the outer glass ply of the windshield, with the first coating being spaced from the second coating. Third and fourth transparent, electroconductive coatings are spaced apart and secured to a flexible, polyester film. The film is positioned between the interlayer and the inner glass ply such that the first coating overlays at least a portion of the third coating and the second coating overlays at least a portion of the fourth coating. The third coating is connected to an electrical signal generator and the fourth coating is connected to an electrical signal receiver so as to form a coupled capacitive circuit with the first and third coatings and the second and fourth coatings each forming a capacitor with the outer glass ply and interlayer operating as a dielectric between the coatings.

In operation, when sufficient moisture accumulates on the windshield sensor so as to bridge the space between the first and second electroconductive coatings, the character of an electrical signal introduced at the third coating and passing through the coupled capacitive circuit will be altered. The altered signal is detected by a signal receiver connected to the fourth coating. In response to the received signal, the windshield wiper motor is activated to clear the outboard surface of the windshield.

DETAILED DESCRIPTION OF THE INVENTION

The present invention is shown with its use in conjunction with a laminated windshield construction, but it should be appreciated that the invention may be used in any application where it is desired to sense surface moisture.

Figure 1:
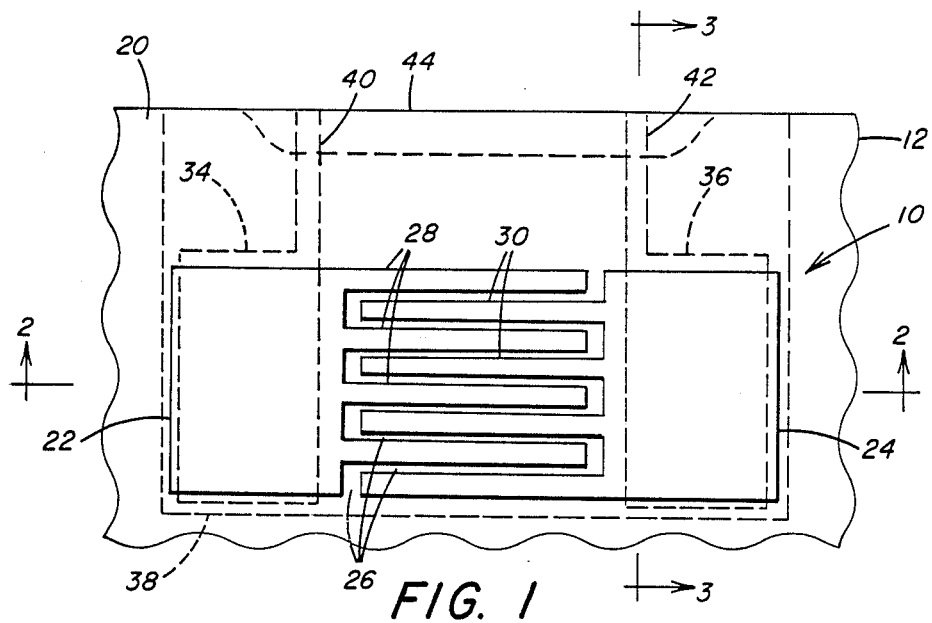
FIG. 1 is a plan view of a capacitive coupled rain sensor incorporating features of the present invention.
Figure 2:
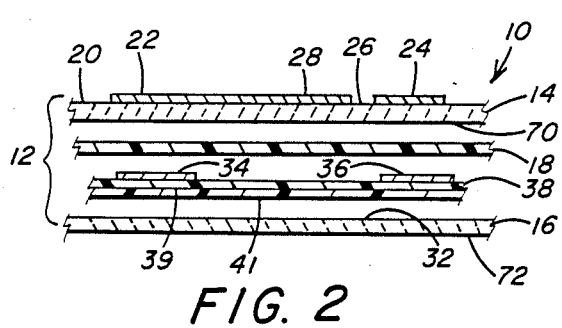
FIG. 2 is a view through line 2—2 of FIG. 1 illustrating the capacitor plates of the present invention.
Figure 3:
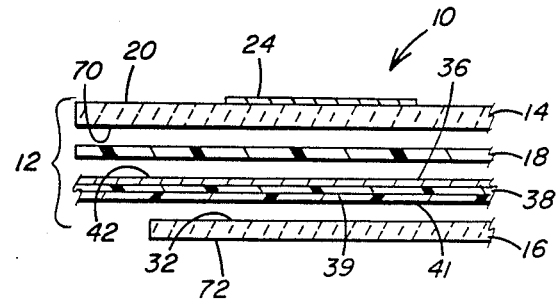
FIG. 3 is a view through line 3—3 of FIG. 1 showing the capacitor plates and an internally positioned lead from the inner plate.

Referring to FIGS. 1 through 3, a rain sensor 10 which is the subject of the present invention is incorporated in a conventional trilayer windshield 12 which includes an outer glass ply 14, inner glass ply 16 and flexible interlayer 18. The sensor 10 may be positioned anywhere on the windshield 12 but preferably is located in an area that is swept by the windshield wipers (not shown) as they clear the viewing area of the windshield.

In the particular embodiment of the invention illustrated in FIGS. 1 through 3, the outer surface 20 of outer ply 14 is coated with two electroconductive film coatings 22 and 24 that are spaced apart and electrically insulated from each other by gap 26 of predetermined width. The gap 26 generally should not be any greater than the width of a small rain drop or mist droplet that may impact or accumulate on the windshield 12 and preferably is in the range of approximately 0.020 inch (0.5 millimeter). Unlike other rain sensors, there is no protective layer over the coatings 22 and 24 so that they are exposed. As a result, the coatings should be abuse resistant, i.e., abrasive, solvent, and weather resistant. The coatings 22 and 24 may be deposited on the outer surface 20 of ply 14 by any well-known coating technique that will not adversely affect the optical quality of the windshield 12, such as a vacuum deposition or pyrolytic deposition. The coatings 22 and 24 may be interdigitated with projections 28 of coating 22 being positioned between and spaced from complementing projections 30 of coating 24. Gap 26 electrically insulates projections 28 from projections 30.

A second set of electroconductive coatings is provided within the windshield 12 and preferably along the surface 32 of the inner ply 16. In the particular embodiment illustrated in FIGS. 1 through 3, coatings 34 and 36 are applied to a flexible carrier 38 such as, for example, a plastic film which is inserted between the inner ply 16 and interlayer 18. In the preferred embodiment, the coatings 34 and 36 are adjacent to the interlayer 18. Surface 39 of the carrier 38 may be provided with an adhesive coating 41 to help prevent delamination of the windshield between carrier 38 and glass ply 16. The coating may be, for example, a pressure sensitive acrylic adhesive or a primer including polyvinylbutyral (2½% by weight) dissolved in methanol. Coatings 34 and 36, which are not necessarily interdigitated, are positioned so as to underlie coatings 22 and 4, respectively, and be spaced therefrom by outer ply 14 and interlayer 18. As with coatings 22 and 24, coatings 34 and 36 are electrically insulated from each other, but unlike coatings 22 and 24, it is not necessary that they be abuse resistant since they are sealed within the windshield 12. The coatings 34 and 36 may be applied by conventional techniques that will not adversely affect the optical properties of the windshield 12 or carrier 38. It should be noted that in an embodiment where the coatings 34 and 36 are applied to a carrier 38 as shown in FIGS. 1 through 3 rather than directly to the surface 32 of inner ply 16, pyrolytic deposition techniques most likely cannot be used since they may distort the carrier 38 resulting in optical defects in the windshield 12 so that vacuum evaporation or magnetic sputtering deposition techniques would be preferred.

Lead members 40 and 42 extend from coatings 34 and 36, respectively, to the edge 44 of the windshield 12 and are electrically connected to an electrical signal generator 46 and an electrical signal receiver 48, respectively, both of which may be incorporated into a controller 50 (shown in FIG. 4) as will be discussed later. In the particular embodiment illustrated in FIG. 1, a portion of the inner ply 16 may be removed along edge 44 to expose the ends of leads 40 and 42 when carrier 38 is pulled away from the interlayer 18 and provide for electrical connection.

In a particular embodiment of the rain sensor, glass plies 14 and 16 are 0.090 inch thick (2.3 millimeters) Solex ® glass and interlayer 18 is 0.030 inch thick (0.8 millimeter) polyvinylbutyral. Coatings 22 and 24 are a transparent tin oxide providing a surface resistivity in the range of approximately 50 to 1000 ohms per square. The flexible carrier 38 is a polyester film approximately 0.0035 inch thick (0.09 millimeter). Coatings 34 and 36 are a transparent metallic film, including silver metal, zinc tin metal, and zinc tin oxide, and providing a resistance of approximately 15 ohms or less per square.

Figure 4:
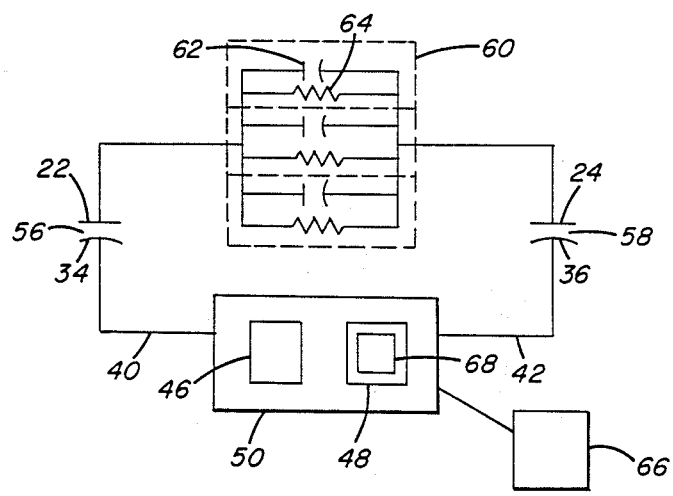
FIG. 4 is a schematic of one type of circuit that may be used with the coupled capacitor rain sensor shown in FIG. 1.

FIG. 4 shows a schematic circuit 54 illustrating the operation of the sensor 10. Coatings 22 and 34 operating as plate members with a dielectric member, i.e., glass ply 14 and interlayer 18, therebetween to form capacitor 56. Similarly, coatings 24 and 36 operate as plate members with dielectric members 14 and 18 therebetween to form capacitor 58. The interdigitated projections 28 and 30 form an impedance network 60. Each pair of adjacent projections operate essentially as a capacitor 62 and a resistor 64 in parallel, as will be discussed later.

A series of signals from the signal generator 46 are inputted into the circuit 54 through lead 40 and the output signal passes through lead 42 to signal receiver 48. Variations in the output signal are monitored by controller 50. When the sensor 10 is dry, the capacitance of capacitor 62 is high and the resistance of resistor 64 is high, so that the impedance network 60 will function essentially like a capacitor, i.e., the signal will pass through circuit 54 principally through capacitor 62, producing an output signal characteristic of the dry condition. However, when water lays on the sensor 10, the capacitance of capacitor 62 decreases and the resistance of resistor 64 drops, so that the impedance network 60 will function essentially like a resistor, i.e., the signal will pass through the circuit 54 principally through resistor 64 producing a different signal characteristic of the wet condition and distinguishable from the dry condition signal.

Although not limiting in the present invention, in one particular embodiment, the monitorable input signal is a series of rectangular voltage pulses. With this input signal, the dry condition output signal is a series of spike-like pulses and the wet condition output signal is a series of attenuated rectangular pulses. Other signals characteristic of the circuit such as current or resistance, may also be used to sense a change from a dry to wet condition and visa versa. Controller 50 activates a windshield wiper motor 66 in response to the wet condition output signal to operate the wipers (not shown) and clear the viewing area of the windshield 12.

When activated, the wiper motor 66 may operate in one of several modes. If desired, the windshield wipers (not shown) may make a single pass across the windshield 12 or they may operate for a given time period or set number of passes. In addition, the electronic circuitry of the windshield wiper controls (not shown) may be such that if the motor 66 is repeatedly activated so as to make a predetermined number of passes within a set time period, the motor 66 will stay activated until it is manually switched off by the vehicle operator.

As more water lays across gap 26 of the sensor 10, an increasing amount of current passes from coating 22 to coating 24 so as to change the selected, monitorable signal of the circuit 54. If desired, the signal receiver 48 or controller 50 may include a sensing circuit 68 that monitors one or more of these signals. By linking the control of a variable speed wiper motor 66 to the sensing circuit 68, the controller 50 can vary the speed of the wipers in response to the output signal received by the sensing circuit 68 so as to automatically control the wiper speed.

It should be appreciated that the lead arrangement in the preferred embodiment of the present invention prevents shorting of the sensor 10 which would result in constant running of the windshield wiper motor. In particular, the leads 40 and 42 extend within the windshield 12 between glass plies 14 and 16 to ensure that they remain electrically insulated from each other so that moisture or salt deposits (which may also form an electrically conductive surface) or the vehicle body (not shown) that surrounds the windshield 12 do not electrically interconnect leads 40 and 42, thus bypassing the capacitors.

It should be further appreciated by one skilled in the art that multiple sensors may be positioned on different portions of the windshield 12 to independently control separate windshield motors. For example, a first sensor may be positioned in the vehicle operator's viewing area and a second sensor in the passenger's viewing area.

In addition, the sensor 10 may be used in a windshield having a bilayer construction (not shown), i.e., a windshield having a single outer glass ply and an inner impact-absorbing antilacerative ply. As with the embodiments shown in FIGS. 1 through 3, the coatings of the sensor 10 would be positioned along the inner and outer surfaces of the glass ply.

Furthermore, the sensor 10 is not limited to use only on the outboard surface of a windshield. For example, the sensor 10 may be used to detect fog or ice on the inboard surface of a vehicle window by locating coatings 22 and 24 on the inboard surface of the glass ply and positioning coatings 34 and 36 at the opposing major surface of the ply, as taught, supra. The sensor 10 would activate a window clearing apparatus such as a window defogger or an electrically heatable window. It should be noted that if coatings 34 and 36 are positioned on a surface exposed to the outside environment, the coatings must be either abuse resistant or protected with an additional abuse resistant coating.

In the present invention, it should be obvious that coatings 34 and 36 are not limited to being positioned between interlayer 18 and ply 16. For example, carrier 38 may be positioned anywhere within the windshield 12, with coatings 34 and 36 being directed toward or away from the adjacent glass ply 14 or 16. Furthermore, the coatings 34 and 36 may be applied directly to surface 70 of the ply 14 with the glass ply 14 operating as the dielectric layer of the capacitors or to surface 72 of ply 16 with the entire windshield 12 operating as the dielectric layer.

Unlike other rain sensors which constantly monitor variations in capacitance caused by moisture absorbant dielectric coatings, there are on protective coatings over the exposed sensor coatings 22 and 24 in the present invention. The sensor 10 of the present invention requires only a monitorable change in the nature of the electrical connection between coatings 22 and 24. As a result, it is important that at least a Portion of coatings 22 and 24 remain exposed so that moisture may bridge gap 26 to alter the circuit 54.

The forms of this invention shown and described in this disclosure represent illustrative embodiments and it is understood that various changes may be made without departing from the scope of the invention as defined in the following claims.

We claim:

1. A sensor for detecting moisture comprising:
a dielectric substrate;
first and second electroconductive members positioned in a fixed, spaced apart relationship relative to each other and adjacent a first major surface of said substrate;
third and fourth electroconductive members positioned in a fixed, space apart relationship relative to each other and adjacent an opposing, second major service of said substrate wherein said first electroconductive member overlays at least a portion of said third electroconductive member and said second electroconductive member overlays at least a portion of said fourth electroconductive member; and
means to provide electrical connection to only said third and fourth electroconductive members.

2. The sensor as in claim 1 wherein said providing means includes means to electrically connect an electrical signal generator to said third conductive member and means to electrically connect an electrical signal receiver to said fourth conductive member.

3. The sensor as in claim 2 further including means responsive to said signal receiver to actuate means to clear said first major surface of said substrate.

4. The sensor as in claim 3 wherein said first and second electroconductive members and said third and fourth electroconductive members are electroconductive coatings secured to said opposing major surfaces of said substrate.

5. The sensor as in claim 4 wherein said substrate and said coatings are transparent.

6. The sensor as in claim 1 wherein said substrate and said electroconductive members are transparent.

7. The sensor as in claim 6 wherein said electroconductive member are metallic coatings.

8. The sensor as in claim 7 wherein said first electroconductive member includes a first set of projections and said second electroconductive member includes a second set of projections wherein said first projections are positioned between and spaced from said second projections.

9. The sensor as in claim 8 wherein said providing means includes means to electrically connect an electrical signal generator to said electroconductive member, and means to electrically connect an electrical signal receiver to said fourth electroconductive member.

10. The sensor as in claim 9 further including means responsive to said signal receiver to actuate means to clear said first major surface of said substrate.

11. The sensor as in claim 10 wherein said clearing means includes a variable speed wiper motor and said signal receiver includes means to sense signal variation in a signal generated by said signal generator whereby the speed of said motor varies in response to said signal variation sensing means.

12. A sensor for detecting moisture comprising:
a dielectric substrate;
first and second electroconductive members positioned in a fixed, spaced apart relationship relative to each other and adjacent a first major surface of said substrate;

third and fourth electroconductive members positioned in a fixed, spaced apart relationship relative to each other and adjacent an opposing, second major surface of said substrate, wherein said first electroconductive member overlays at least a portion of said third electroconductive member and said second electroconductive member overlays at least a portion of said fourth electroconductive member; and at least one additional substrate secured in a fixed relationship to said second major surface of said substrate to form a composite assembly.

13. The sensor as in claim 12 wherein said first and second electroconductive members are secured to said first major surface of said substrate.

14. The sensor as in claim 13 wherein said third and fourth electroconductive members are secured to a major surface of one of said additional substrates.

15. The sensor as in claim 14 further including means to provide electrical connection only to said third and fourth electroconductive members.

16. The sensor as in claim 15 wherein said substrates and said electroconductive members are transparent.

17. The sensor as in claim 13, wherein said third and fourth electroconductive members are secured to a flexible carrier positioned adjacent to said second major surface of said first substrate.

18. The sensor as in claim 17 wherein said flexible carrier is a polyester film.

19. The sensor as in claim 18 further including a means to provide electrically connection only to said third nd fourth electroconductive members.

20. The sensor as in claim 19 wherein said substrates, said flexible carrier, and said electroconductive members are transparent.

21. The sensor as in claim 13 wherein said additional substrates include an interlayer secured to said second major surface of said first substrate and a second substrate with a first major surface secured to a second major surface of said interlayer and further wherein said third and fourth electroconductive members are positioned between said interlayer and said second substrate.

22. The sensor as in claim 21 further including means to provide electrical connection only to said third and fourth electroconductive members, said third and fourth electroconductive members are positioned between said interlayer and said second substrate.

23. The sensor as in claim 22 wherein said first electroconductive member includes a first set of projections and said second electroconductive member includes a second set of projections wherein said first projections are positioned between and spaced from said second projections.

24. The sensor as in claim 23 wherein said third and fourth electroconductive members are secured to a flexible carrier positioned between said interlayer and second substrate.

25. The sensor as in claim 24 further including an adhesive coating between said flexible carrier and said second substrate.

26. The sensor as in claim 24 wherein said flexible carrier is an polyester film.

27. The sensor as in claim 24 wherein said substrates, said flexible carrier, and said electroconductive members are transparent.

28. The sensor as in claim 27 wherein said providing means includes means to electrically connect an electrical signal generator to said third electroconductive member and means to electrically connect an electrically signal receiver to said fourth electroconductive member.

29. The sensor as in claim 28 further including means responsive to said signal receiver to actuate means to clear said first major surface of said first substrate.

30. The sensor as in claim 29 wherein said clearing means includes a variable speed wiper motor and said signal receiver includes means to sense signal variation in a signal generated by said signal generator whereby the speed of said motor varies in response to said signal variation sensing means.

31. The sensor as in claim 30 wherein said composite assembly is a vehicle windshield and said first major surface of said first substrate is the outboard surface of said windshield.

* * * * *

UNITED STATES PATENT AND TRADEMARK OFFICE
CERTIFICATE OF CORRECTION

PATENT NO. : 4,805,070

DATED : February 14, 1989

INVENTOR(S) : HARRY S. KOONTZ AND JAMES F. WILSON

It is certified that error appears in the above-identified patent and that said Letters Patent is hereby corrected as shown below:

Claim 9, line 3, after "said" insert --third--.

Claim 19, line 1, delete "a"; line 3, delete "nd" and insert --and--.

Claim 22, line 3, after "members" delete --, said third...second substrate--.

Signed and Sealed this

Twenty-fourth Day of July, 1990

*Attest:*

HARRY F. MANBECK, JR.

*Attesting Officer*      *Commissioner of Patents and Trademarks*